(12) United States Patent
Turley et al.

(10) Patent No.: US 6,537,978 B1
(45) Date of Patent: *Mar. 25, 2003

(54) ORAL ADMINISTRATION OF EFFECTIVE AMOUNTS OF FORMS OF HYALURONIC ACID

(75) Inventors: Eva A Turley, Toronto (CA); Samuel S Asculai, Toronto (CA)

(73) Assignee: Jagotec AG, Muttenz (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/101,286

(22) PCT Filed: Jan. 8, 1997

(86) PCT No.: PCT/CA97/00007

§ 371 (c)(1),
(2), (4) Date: Jul. 6, 1998

(87) PCT Pub. No.: WO97/25051

PCT Pub. Date: Jul. 17, 1997

(30) Foreign Application Priority Data

Jan. 11, 1996 (CA) .............................................. 2167044
Dec. 24, 1996 (CA) .............................................. 2193921

(51) Int. Cl.$^7$ ................................................ A61K 31/70
(52) U.S. Cl. ....................................................... 514/54
(58) Field of Search ........................................... 514/54

(56) References Cited

U.S. PATENT DOCUMENTS 4,840,941 A * 6/1989 Uero et al. .................... 514/59
5,614,506 A * 3/1997 Falk et al. ..................... 574/55

FOREIGN PATENT DOCUMENTS

| WO | WO 91/04058 | 4/1991 |
| WO | WO 93/23059 | 11/1993 |
| WO | WO 94/07505 A1 | 4/1994 |
| WO | WO 95/26193 | 10/1995 |

* cited by examiner

*Primary Examiner*—Elli Peselev
(74) *Attorney, Agent, or Firm*—Leydig Voit & Mayer Ltd.

(57) ABSTRACT

This invention relates to the oral administration of forms of hyaluronic acid (for example hyaluronan (hyaluronic acid) and pharmaceutically acceptable salts thereof such as sodium hyaluronate), and orally administrable dosage forms containing forms of hylruonic acid, for the prevention and/or treatment of diseases and/or conditions such as the prevention of restenosis and the treatment of an infarct (heart attack) or a stroke. The oral administration and the orally administered dosage forms may also include therapeutic agents and/or medicines which may be administered orally for the treatment and/or prevention of the diseases and/or conditions with the forms of hyaluronic acid (hyaluronan) previously described.

35 Claims, 19 Drawing Sheets

|  | Time in Hours | Amounts | Amount in Rat Blood Stream ng/ml (µg/L) |
|---|---|---|---|
| ORAL 30mg/kg | 4 | 933<br>549<br>2178 | 1220.00 M<br>695.31 SD<br>401.44 SE |
|  | 8 | 502<br>1964<br>1004 | 1156.67 M<br>606.54 SD<br>350.19 SE |
|  | 12 | 1668<br>1973<br>1872 | 1837.67 M<br>126.86 SD<br>73.24 SE |
|  | 24 | 2280<br>2008<br>1667 | 1985.00 M<br>250.78 SD<br>144.79 SE |
|  | 48 | 6336<br>3557<br>981 | 3624.67 M<br>2186.69 SD<br>1262.49 SE |
|  | 72 | 4187<br>1057<br>2985 | 2743.00 M<br>1289.22 SD<br>744.33 SE |

FIG. 9A

|  | Time in Hours | Amounts | Amount in Rat Blood Stream ng/ml (µg/L) |
|---|---|---|---|
| ORAL 10mg/kg | 3 | 267.7<br>256.8<br>1442.9 | 655.80 M<br>556.58 SD<br>321.34 SE |
|  | 7 | 1284.7<br>122.5 | 703.60 M<br>581.10 SD<br>410.90 SE |
|  | 12 | 458<br>261 | 359.50 M<br>98.50 SD<br>69.65 SE |
|  | 24 | 1018.1<br>2378 | 1698.05 M<br>679.95 SD<br>480.80 SE |
|  | 48 | 2981.7<br>3516.3 | 3249.00 M<br>267.30 SD<br>189.01 SE |
|  | 72 | 2491.9<br>2892 | 2691.95 M<br>200.05 SD<br>141.46 SE |

FIG. 9B

|  | Time in Hours | Amounts | Amount in Rat Blood Stream ng/ml (µg/L) |
|---|---|---|---|
| ORAL 3mg/kg | 4 | 225<br>524<br>906 | 551.67 M<br>278.70 SD<br>160.91 SE |
|  | 8 | 3822<br>2592<br>1175 | 2529.67 M<br>1081.53 SD<br>624.42 SE |
|  | 12 | 2029<br>695<br>1366 | 1363.33 M<br>544.61 SD<br>314.43 SE |
|  | 24 | 1139<br>933<br>2569 | 1547.00 M<br>727.54 SD<br>420.05 SE |
|  | 48 | 735<br>905<br>236 | 625.33 M<br>283.91 SD<br>163.92 SE |
|  | 72 | 501<br>6844<br>3758 | 3701.00 M<br>2589.83 SD<br>1495.24 SE |

FIG. 9C

Reflects use of same originally administered Hyaluronan (HA) as that used for determining molecular weight by Dextran Standard in Figure 12B.

Dextran Standards

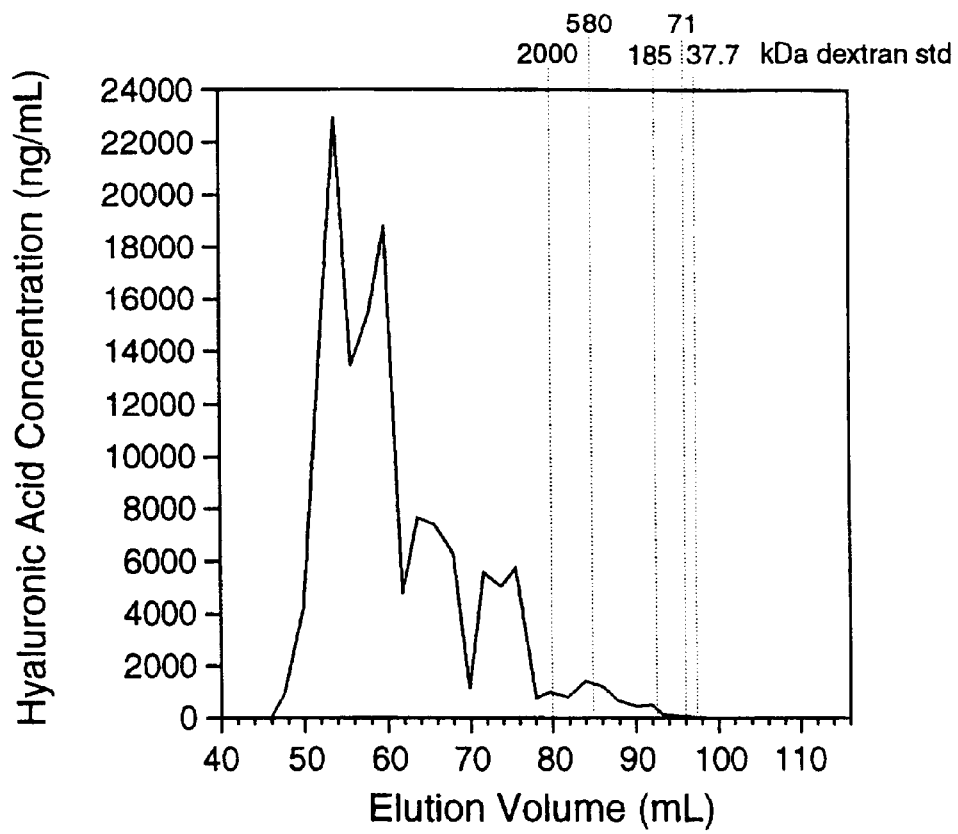

Hyaluronic Acid (mol. wt. 300-500kDa)
on Sephacryl 500-HR 1.6x61.5 cm Column

- hyaluronic acid (Hyal Corp.) 10 mg/mL
- diluted 1:100 (.05M phosphate buffer, .15M NaCL, 5% sucrose)
- filtered MillexHv13, .45μm
- 1.5mL applied
- 2.0mL (68 drops) fractions collected
- flow rate 0.42mL/min.
- column #1

Use of same originally administered Hyaluronan (Ha) as that used for determining molecular weight by Protein Standard in Figure 12A.

FIG. 12B

ORAL ADMINISTRATION OF EFFECTIVE AMOUNTS OF FORMS OF HYALURONIC ACID

This application is a U.S. National Phase Application of PCT/CA97/00007, filed on Jan. 8, 1997, which claims priority to Canadian Applications 2,167,044, filed on Jan. 11, 1996, and 2,193,921, filed on Dec. 24, 1996.

FIELD OF INVENTION

This invention relates to the oral administration of forms of hyaluronic acid (for example hyaluronan (hyaluronic acid) and pharmaceutically acceptable salts thereof such as sodium hyaluronate), and orally administrable dosage forms containing forms of hyaluronic acid, for the prevention and/or treatment of diseases and/or conditions such as the prevention of restenosis and the treatment of an infarct (heart attack) or a stroke. The oral administration and the orally administered dosage forms may also include therapeutic agents and/or medicines which may be administered orally for the treatment and/or prevention of the diseases and/or conditions with the forms of hyaluronic acid (hyaluronan).

BACKGROUND OF THE INVENTION

In International Publication WO95/26193 (Application PCT/CA94/00188), hyaluronic acid and/or pharmaceutically acceptable salts thereof are administered to prevent restenosis of the arterial walls when the artery walls are traumatized by for example balloon angioplasty.

Generally a newborn's arteries each consist of the outer adventitia and inner intima. The inner surface of the intima presents an elastic lamina. As the newborn grows into an adult human, a neointima (made of migrating smooth muscle cells, leucocytes (macrophages) and fat deposited in the leucocytes (macrophages)(in foamy cells)), develops radially inwardly of the intima, thus narrowing or constricting the opening in the artery (stenosis). This narrowing or constriction reduces blood flow. The development of the neointima depends on the human's diet, physical conditioning and physical and genetic make-up.

In some people, the size of the neointima has substantially constricted the blood flow through the artery, jeopardizing the human's life. In an attempt to reduce/alleviate the effects of the size of the neointima and its affects on the human, balloon angioplasty is performed reducing the radial inward extent of the neointima. However in a substantial number of the humans receiving this procedure, restenosis of the artery occurs by migration of the smooth muscle cells to, and concentration of leucocytes carrying fat deposits at, the place of the balloon angioplasty thus increasing the radial inward extent of the neointima.

The teachings of publication WO95/26193 provide a procedure for preventing restenosis using forms of hyaluronic acid administered before, during and/or after the balloon angioplasty procedure. Suitable amounts may be administered intravenously, by injection, or subcutaneously. The form of hyaluronic acid preferably had a molecular weight of less than 750,000 daltons and in one embodiment a concentration of about 2% by weight in sterile water. Effective amounts of the form of hyaluronic acid provided in each dosage administered were from about 10 mg/70 kg human to in excess of 3000 mg/70 kg person, prior to, during and/or after the angioplasty procedure. The oral route was not given as one of the preferred routes. The reason is that persons skilled in the art generally believe that oral administration of the form of hyaluronic acid will not at least for small amounts pass the form of hyaluronic acid into the blood system from the stomach. Such persons believe that a substantial portion of any orally administered form of hyaluronan will be digested, degraded or disassociated into its smaller sugar components in the stomach by the stomach acid before a substantial amount of the form of hyaluronan (greater than K (1000) daltons) can enter the blood system. Thus according to the beliefs of pesons skilled in the art, very large dosage amounts of the form of hyaluronan would have to be administered orally for oral delivery to be effective, and even then consider it unlikely to escape the stomach as intact high molecular weight HA.

Publication WO91/04058 (Application PCT/CA90/00306) teaches the use of a minimum amount of 10 mg/70 kg person of a form of hyaluronan up to in excess of 3000 mg/70 kg person to transport medicines and/or therapeutic agents to the site in the human body in need of the treatment, with preferred amounts exceeding 50 mg/70 kg person to about 350 mg/70 kg person [Page 26, lines 32–37]. At page 18, reference is made to the proposed routes of administration. One of the routes proposed to be used is by oral administration [Page 18, line 5]. However not one of the specific examples in the document, provides specifics using the oral route. At that time oral administration was thought not to be that efficient. While the oral route may have been proposed, persons skilled in the art would believe much of the administered form of hyaluronan would not pass intact into the blood stream. Therefore persons skilled in the art would prefer the other routes for example, intravenous and direct injection when employing the teachings of the document.

Hence Applicants herein believe that oral administration of forms of hyaluronan would not be preferred by persons skilled in the art or in fact be used because to their minds there are better alternate routes. For example the routes of administration of the hyaluronic acid as taught by U.S. Pat. No. 4,808,576 are intramuscular, intravenous, subcutaneous and topical (Column 3, lines 17–18). No teaching of oral administration of hyaluronic acid is proposed as it was believed at that time (even to the present date) that oral administration would not be as good a route.

Thus Applicants believe that the preferred routes of administration to persons skilled in the art are systemic (intravenous, direct injection), subcutaneous and most recently topical. However systemic administration requires hospital or medical clinic time for administration—a costly procedure even under "out-patient" treatment conditions. If the patient in the hospital were to be treated by intravenous administration or by subcutaneous injection over for example 3–5 days, the costs can be substantial. For many conditions, topical treatment is not appropriate.

It is therefore an object of this invention to provide for the prevention and/or treatment of diseases and/or conditions by the oral administration of forms of hyaluronic acid (hyaluronan).

It is a still further object of the invention to provide orally administrable dosages containing forms of hyaluronan which allow the orally administrable form of intact hyaluronan in the stomach prior to passage into the blood stream, in a biologically active form (35,000 daltons to 2,000,000 daltons) determined by the Dextran Standard. (The conversion factor from the newer Dextran Standard to the older Protein Standard on which earlier filed applications were based, is in the order of about 3.3. The molecular weight determined under the newer Dextran Standard must be divided by 3.3 to determine the molecular weight under the older Protein Standard. Thus, the above molecular weights would be between about 11,000 daltons to about 600,000 K. daltons.)

It is a further object of the invention to provide dosages containing forms of hyaluronan for oral administration.

Further and other objects of the invention will be realized by those skilled in the art from the following summary of the invention and detailed discussion of embodiment thereof.

SUMMARY OF THE INVENTION

In the development of this invention, the inventors have discovered:

(a) that unexpectedly, hyaluronan when administered orally can be effective to treat and/or prevent a condition and/or disease of a human, such as prevent restenosis;

(b) that unexpectedly "more" hyaluronan is not necessarily better and that unexpectedly "less" hyaluronan may be better (for example dosage amounts between about 3 mg/kg of body weight of a human to about 100 mg/kg of a human of a form of hyaluronan and preferably between about between 3 mg/kg to about 30 mg/kg of a human and more preferably between about 3 mg/kg to about 10 mg/kg for example to prevent restenosis, is preferred (the effect of the administered dosage amounts of the form of hyaluronan thereby being "phasic")); and (c) that unexpected molecular weight distributions of the form of hyaluronan, ranging from 30,000 to greater than 70,000 daltons (determined by the well known Protein Standard), and in the human between 30,000 to 2,000,000 daltons using the Dextran Standard (which is believed to be more accurate) are the molecular weights of the form of hyaluronan that appear in plasma after administered orally (for example comprising a solution of 2% sodium hyaluronate by weight in sterile water) preventing minimal degradation by the human body when given orally, compared to subcutaneous or intravenous administration. [Once again, conversion of the molecular weight determined by the Dextran Standard must be divided by the conversion factor which factor is in the order of about 3.3. Thus the molecular weights of 30,000 to 2,000,000 daltons using the Dextran Standard correspond from about 9,000 daltons to about 600,000 daltons in the older Protein Standard.]

Therefore new dosages for administration to humans, each dosage containing forms of hyaluronan which the human body can easily use (by delivering the form of hyaluronan directly from the stomach into the blood stream) may comprise in suitable form (preferably liquid form) for oral administration in a suitable excipient (for example sterile water), at least one of the following:

(i) between about 3 mg of the form of hyaluronan/kg to about 100 mg of the form of hyaluronan/kg of body weight of the human taking the oral dose form, in the oral dosage form (preferably between about 3 mg/kg and about 30 mg/kg of the human of the form of hyaluron and more preferably the amount of the form of hyaluronan is between about 3 mg/kg to about 10 mg/kg of the body weight of the human taking the oral dosage) and (ii) the form of hyaluronan in the orally administrable dosage form having a mean average molecular weight distribution in the range selected from the following group of ranges, (a) between about 30,000 to 2,000,000 daltons is detected by Dextran Standards (which corresponds to between about 9,000 daltons and about 600,000 daltons delivered by the Protein Standard using the conversion factor of about 3.3), and (b) about 30,000 to greater than 70,000 daltons as detected by the Protein Standards.

(for example as a 2% by weight solution of hyaluronan in sterile water).

Therefore new methods of treatment and/or prevention of a disease and/or condition, for example prevention of restenosis, is provided comprising orally administering an effective amount of an orally administrable pharmaceutical dosage form comprising the form of hyaluronan for such period of time as required (including any maintenance therapy). For example for the prevention of restenosis the oral administration of a dosage according to the invention may take place before, during and/or after balloon angioplasty, The dosage is constituted according to the above new dosages. Thereafter the oral administration of the oral dosages takes place as needed (for example to prevent restenosis after balloon angioplasty, oral administration may take place for a period of 3–5 days after the balloon angioplasty procedure as maintenance therapy). This administration can be carried out by patients at home simply following their doctors' instructions by taking their oral dosages.

The form of hyaluronan may comprise hyaluronic acid and/or pharmaceutically acceptable salts thereof, for example, sodium hyaluronate.

Where the form of hyaluronic acid used in the oral dosage form does not have a molecular weight in the ranges specified above in subparagraph (ii) (a), (b) or (c), the form of hyaluronan preferably has a molecular weight less than 750,000 daltons (Protein Standard), for example 400,000 daltons (Protein Standard) in the amounts specified in subparagraph (i) above.

One form of hyaluronic acid and/or pharmaceutically acceptable salts thereof suitable for use is a fraction supplied by Hyal Pharmaceutical Corporation (Applicant herein). One such amount is a 15 ml vial of Sodium hyaluronate 20 mg/ml (300 mg/vial—Lot 2F3). The sodium hyaluronate fraction is a 2% solution with a mean average molecular weight distribution of about 225,000 daltons (Protein Standard). The amount also contains water q.s. which is triple distilled and sterile in accordance with the U.S.P. for injection formulations. The vials of hyaluronic acid and/or pharmaceutically acceptable salts thereof may be carried in a Type 1 borosilicate glass vial closed by a butyl stopper which does not react with the contents of the vial.

Many forms of hyaluronan may be suitable for use herein. Particularly, molecular weights of forms of hyaluronan between about 150,000 daltons (Protein Standard) and about 750,000 daltons (Protein Standard) in sterile water prepared having a viscosity for intravenous administration are suitable.

One specific form of pharmaceutical grade is a 1% sterile sodium hyaluronate solution (50 ml vials) provided by Hyal Pharmaceutical Corporation which has the following characteristics:

| Tests | Specifications |
| --- | --- |
| 1. Container Description | 1 50 mL Flint glass vial with a red or gray rubber stopper and an aluminum seal, 20 mm in size. |

-continued

| Tests | Specifications |
| --- | --- |
| 2. Product Description | A clear, colourless, odourless, transparent, slightly viscous liquid. |
| 3. Fill Volume | 50.0 to 52.0 mL |
| 4. pH | 5.0 to 7.0 at 25 degrees C. |
| 5. Specific Gravity | 0.990 to 1.010 at 25 degrees C. |
| 6. Intrinsic Viscosity | 4.5 to 11.0 dL/g |
| 7. Molecular Weight | 178,000 to 562,000 daltons |
| 8. Sodium Hyaluronate Assay and Identification | 9.0 to 11.0 mg/mL. Positive |
| 9. Particulate Matter | No visible Particulate Matter |
| 10. Sterility | Meets Requirements for Sterility, USP 23 |
| 11. Bacterial Endotoxins (LAL) | Meets Requirements for Bacterial Endotoxins, USP 23. |

This pharmaceutical grade 1% sterile solution of hyaluronan may be made from granules/powder having the following characteristics:

| Tests | Specifications |
| --- | --- |
| 1. Description | White or cream-coloured granules or powder, odourless |
| 2. Identification (IR Spectrum) | Must conform with the Reference Standard Specturm. |
| 3. pH (1% Solution) | Between 5.0 and 7.0 at 25 degrees C. |
| 4. Loss on Drying | NMT 10.0% at 102 degrees C. for 6 hours. |
| 5. Residue on Ignition | Between 15.0 and 19.0% |
| 6. Protein Content | NMT 0.10% |
| 7. Heavy Metals | NMT 20 ppm (as per USP 23 p. 1727). |
| 8. Arsenic | NMT 2 ppm (as per USP 23, p. 1724). |
| 9. Residual Solvents | a) Acetone: NMT 0.1% b) Ethanol: NMT 2.0% c) Formaldehyde: NMT 100 ppm |
| 10. Sodium Hyaluronate Assay | 97.0 to 102.0% (dried basis) |
| 11. Intrinsic Viscosity | Between 10.0 to 14.5 deciliters per gram. |
| 12. Molecular Weight (calculated using the Laurent Formula) | Between 500,000 to 800,000 daltons (based on intrincis viscosity). |
| 13. Total Aerobic Microbial Count | NMT 50 microorganism/gram (as per USP 23, p. 1684). |
| 14. Test for *Escherichia coli* | *Escherichia coli* is absent (as per USP) 23, p. 1685). |
| 15. Yeasts & Molds | NMT 50 microorganisms/gram (as per USP 23, p. 1686). |
| 16. Endotoxins (LAL) | NMT 0.07 EU/mg (as per USP 23, p. 1696). |

A topical grade of hyaluronan (which may be sterilized) may, in certain circumstances be suitable and may be made from the following granules/powder which have the following characteristics:

| Tests | Specifications |
| --- | --- |
| 1. Description | White or cream-coloured granules or powder, odourless |
| 2. Identification (IR Spectrum) | Must conform to the Reference Standard Specturm. |
| 3. pH (1% Solution) | Between 6.0 and 8.0 at 25 degrees C. |
| 4. Loss on Drying | NMT 10.0% at 102 degrees C. for 6 hours. |
| 5. Residue on Ignition | Between 15.0 and 19.0% |
| 6. Protein Content | NMT 0.40% |
| 7. Heavy Metals | NMT 20 ppm (as per USP 23 p. 1727). |
| 8. Arsenic | NMT 2 ppm (as per USP 23, p. 1724). |
| 9. Residual Solvents | a) Acetone: NMT 0.1% b) Ethanol: NMT 2.0% c) Formaldehyde: NMT 100 ppm |
| 10. Sodium Hyaluronate Assay | 97.0 to 102.0% (dried basis) |
| 11. Intrinsic Viscosity | Between 11.5 to 14.5 deciliters per gram. |
| 12. Molecular Weight (calculated using the Laurent Formula) | Between 600,000 to 800,000 daltons (Protein Standard) (based on intrinsic viscosity). |
| 13. Total Aerobic Microbial Count | NMT 100 microorganism/gram (as per USP 23, p. 1684). |
| 14. Test for *Staphylococcus aureus* | *Staphylococcus aureus* is absent (as per USP 23, p. 1684). |
| 15. Test for *Pseudomonas aeruginosa* | *Pseudomonas aeruginosa* is absent (as per USP 23, p. 1684). |
| 16. Yeasts & Molds | NMT 200 CFU/gram (as per USP 23, p. 1686). |

This topical grade may then be sterilized.

Other forms may be suitable such as one form of hyaluronic acid and/or pharmaceutically acceptable salts thereof (for example, sodium salt) may be an amount also supplied by Hyal Pharmaceutical Corporation. One such amount is a 15 ml vial of Sodium hyaluronate 20 mg/ml (300 mg/vial—Lot 2F3). The sodium hyaluronate fraction is a 2% solution with a mean average molecular weight of about 225,000 (Protein Standard). The amount also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with contents of the vial.

The amount of hyaluronic acid and/or salts thereof (for example sodium salt) may comprise hyaluronic acid and/or salts thereof having the following characteristics:

a purified, substantially pyrogen-free fraction of hyaluronic acid obtained from a natural source having at least one characteristic selected from the group consisting of the following:
  i) a molecular weight within the range of 150,000–225,000 (Protein Standard);
  ii) less than about 1.25% sulphated mucopolysaccharides on a total weight basis;
  iii) less than about 0.6% protein on a total weight basis;
  iv) less than about 150 ppm iron on a total weight basis;
  v) less than about 15 ppm lead on a total weight basis;
  vi) less than 0.0025% glucosamine;
  vii) less than 0.025% glucuronic acid;
  viii) less than 0.025% N-acetylglucosamine;
  ix) less than 0.0025% amino acids;
  x) a UV extinction coefficient at 257 nm of less than about 0.275;
  xi) a UV extinction coefficient at 280 nm of less than about 0.25; and,
  xii) a pH within the range of 7.3–7.9. Preferably, the hyaluronic acid is mixed with water and the fraction of hyaluronic acid fraction has a mean average molecular weight within the range of 150,000–225,000 (Protein Standard).

Preferably this amount of hyaluronic acid comprises at least one characteristic selected from the group consisting of the following characteristics:

i) less than about 1% sulphated mucopolysaccharides on a total weight basis;
ii) less than about 0.4% protein on a total weight basis;
iii) less than about 100 ppm iron on a total weight basis;
iv) less than about 10 ppm lead on a total weight basis;
v) less than 0.00166% glucosamine;
vi) less than 0.0166% glucuronic acid;
vii) less than 0.016% N-acetylglucosamine;
viii) less than 0.00166% amino acids;
ix) a UV extinction coefficient at 257 nm of less than about 0.23;
x) a UV extinction coefficient at 280 nm of less than 0.19; and
xi) a pH within the range of 7.5–7.7

Other forms of hyaluronic acid and/or its salts may be chosen from other suppliers, for example those described in prior art documents disclosing forms of hyaluronic acid having lower molecular weights between about 150,000 daltons and 750,000 daltons being prepared as for example, 1–2% solutions in sterile water for intravenous administration. In addition, sodium hyaluronate produced and supplied by LifeCore™ Biomedical, Inc. having the following specifications may be suitable (if sterile):

| Characteristics | Specification |
| --- | --- |
| Appearance | White to cream colored particles |
| Odor | No perceptible odor |
| Viscosity Average Molecular Weight | <750,000 Daltons (Protein Standard) |
| UV/Vis Scan, 190–820 nm | Matches reference scan |
| OD, 260 nm | <0.25 OD units |
| Hyaluronidase Sensitivity | Positive Response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |

Heavy Metals, maximum ppm

| As | Cd | Cr | Co | Cu | Fe | Pb | Hg | Ni |
| --- | --- | --- | --- | --- | --- | --- | --- | --- |
| 2.0 | 5.0 | 5.0 | 10.0 | 10.0 | 25.0 | 10.0 | 10.0 | 5.0 |

| | |
| --- | --- |
| Microbial Bioburden | None observed |
| Endotoxin | <0.07 EU/mg NaHy |
| Biological Safety Testing | Passes Rabbit Ocular Toxicity Test |

The following references teach hyaluronic acid, sources thereof and processes of the manufacture and recovery thereof.

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 (Protein Standard) and discusses processes of their manufacture.

Where high molecular weight hyaluronic acid (or salts or other forms thereof) is used, it must, prior to use, be diluted to permit administration and ensure no intramuscular coagulation. (Preferably they should be autoclaved to reduce their molecular weight.) Recently, it has been found that large molecular weight hyaluronic acid having a molecular weight exceeding about 1,000,000 daltons self-aggregates and thus, does not interact very well with HA receptors. Thus, the larger molecular weight hyaluronic acid should be avoided (such as Healon™).

For making the oral dosage forms more pleasant to take taste enhancers or flavours may be added to make the taking more pleasant provided the form of the hyaluronan is not adversely affected (degraded, disassociated or bound up with other materials so as not to be suitable herein). Additionally the dosages may be mixed with a drink liquid to be more enjoyable to take provided the form of hyaluronan is not adversely affected. The dosages may also be taken straight (without their addition to any drink) as there is really no unpleasant flavour.

The invention relates to oral dosages containing forms of hyaluronan and the oral administration thereof to treat or prevent a disease or condition. Thus, the invention can be used for restenosis prevention and other treatments in the same manner that hyaluronan is used. Thus, the invention can be used for the treatments and preventative therapies discussed in the following published and unpublished documents identified below and for the purposes in Canadian Patent Application Serial No. 2,164,260, filed in the Canadian Patent Office on the 1st day of December, 1995 entitled "Targeting of Dosages of Medicines and Therapeutic Agents", and Canadian Patent Application Serial Number 2,173,037, filed on the 29th day of March, 1996 entitled "Targeting of Dosages of Medicines and Therapeutic Agents and other Glycosaminoglycans (GAGS)", each of which documents is incorporated herein by reference: (with respect to the teachings of each of the documents, the dosages of hyaluronan may be substituted by the oral dosages referred to herein and be used in like manner)

| PCT Application | International Publication | U.S. Application |
| --- | --- | --- |
| PCT/CA90/00306 | WO 91/04058 | Ser. No. 07/675,908 |
| PCT/CA93/00061 | WO 93/16732 | Ser. No. 08/290,840 |
| PCT/CA93/00062 | WO 93/16733 | Ser. No. 08/290,848 |
| PCT/CA93/00388 | WO 94/07505 | Ser. No. 07/952,095 |
| PCT/CA94/00207 | WO 94/23725 | Ser. No. 08/448,504 |
| PCT/CA95/00243 | WO 95/29683 | Ser. No. 08/464,769 |
| PCT/CA94/00188 | WO 95/26193 | Ser. No. 08/448,503 |
| PCT/CA95/00259 | WO 95/30423 | Ser. No. 08/464,768 |
| PCT/CA95/00467 | | Ser. No. 08/295,390 |
| PCT/CA95/00477 | | Ser. No. 08/468,328 |

As an example, I have extracted from Application PCT/CA90/00306 (International Publication No. WO 91/04058) the following to illustrate just some of the uses:

(i) at page 17, line 3 to page 18, line 16:
"Applicants have now discovered that combinations and formulations (for example an injectable formulation) can be provided for administration to a mammal for the treatment of a disease or condition, which combinations or formulations employ or incorporate as the case may be a therapeutically effective non-toxic amount of a medicinal and/or therapeutic agent to treat the disease or condition (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol9-[nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/−) tromethamine salt of ketorolac (sold under the trademark Toradol™) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark Lasix™)), immunosuppressants (for example cyclosporins), lymphokynes (such as interleukin—2 and the like), alpha-and-β-interferon and the like) administered with, or carried in, an amount of hyaluronic acid and/or salts thereof (for example the sodium salt) and/or homologues, analogues, derivatives, complexes, esters, fragments, and/or sub units of hyaluronic acid (preferably hyaluronic acid and salts thereof) sufficient to facilitate the agent's penetration through the tissue (including scar tissue), at the site to be treated through the cell membranes into the individual cells to be treated. When such combinations and formulations are administered to patients suffering from the disease or condition, the disease or condition is unexpectedly improved.

The formulation can be administered among other methods, intravenously, intra arterially, intraperitoneally, intrapleurally, transdermally, on the skin (topically), rectally, orally or by direct injection (for example into a tumor, into an abscess or similar disease focus) or put on a patch to be secured to the skin of the patient. The hyaluronic acid and/or salts thereof and the agent can be administered separately but are administered in sufficient amounts and in an immediate time sequence or interval (preferably concurrently and more preferably simultaneously), preferably at the identical site (e.g. one given intravenously and the other "piggy backed"), to treat the disease or condition."

Thus this invention also provides oral dosages comprising effective amounts of the forms of hyaluronan herein described with effective amounts of medicines and/or therapeutic agents and the oral administration of these oral dosages for the treatment and prevention of disease and/or conditions of the human body.

The invention will now be illustrated with reference to the following Figures and Detailed Description of Embodiments:

BRIEF DESCRIPTION OF THE DRAWINGS

FIG. 6 presents a series of photos of stenosis following Hyaluronan (HA) administration of rats wherein:

FIGS. 9A, 9B and 9C illustrate in tabular form the concentration of hyaluronan in rat blood serum after oral administration of various amounts of hyaluronan (m.w. less than 750,000 daltons determined by Protein Standard).

FIGS. 12A and 12B each depict standard curve for the same originally administered HA as detected by protein standards [FIG. 12A] and dextran standards [FIG. 12B].

DETAILED DESCRIPTION OF EMBODIMENTS

Figure 2:
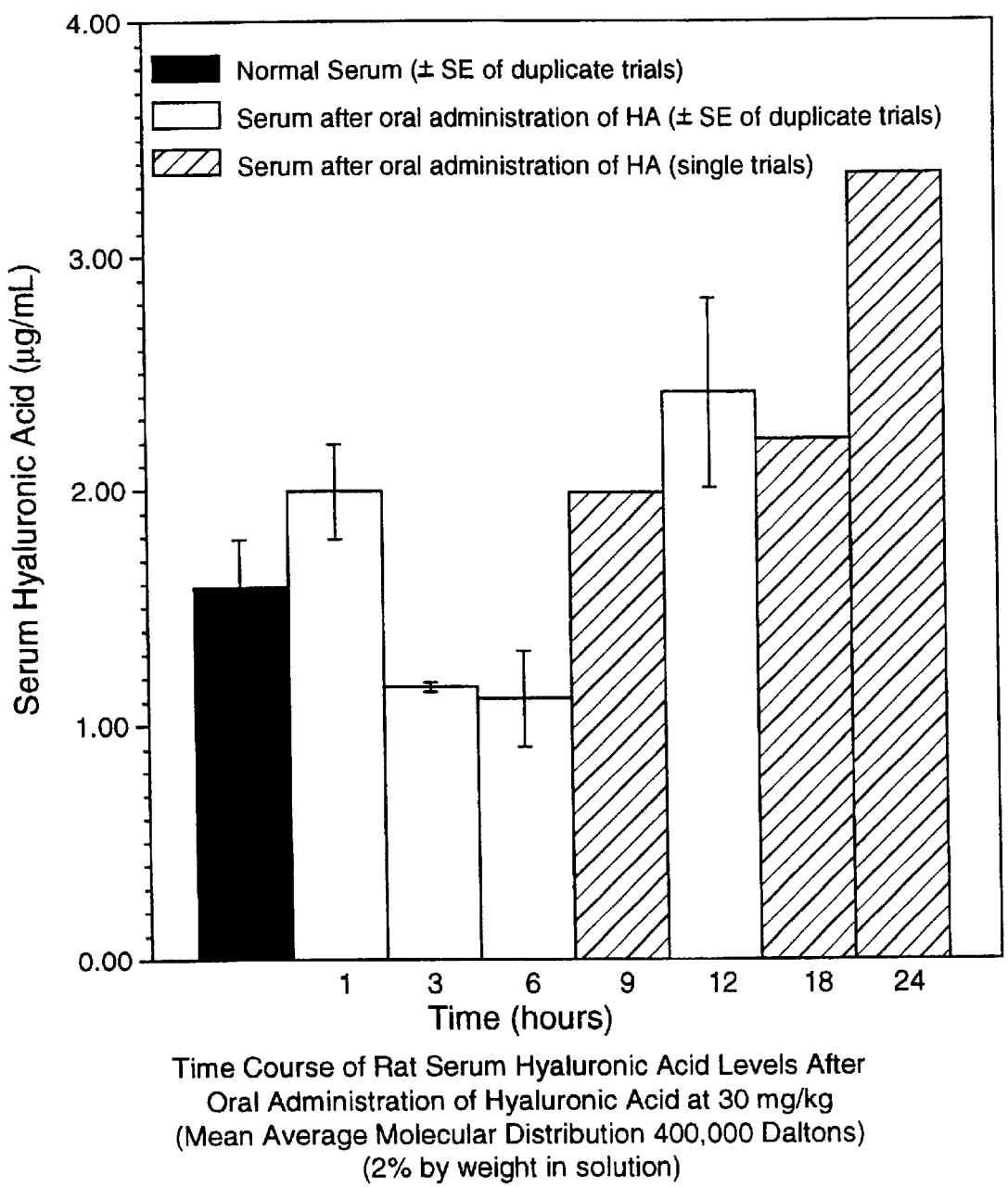
FIG. 2 illustrates a summary of Time Course of Rat Serum HA levels after oral administration of Hyaluronic Acid at 30 mg/kg (Mean Average Molecular Weight Distribution of 400,000 daltons (Protein Standard) (2% by weight in solution 30,000 to greater than 70,000 daltons (30→70 kDa) (using protein standards)).

FIG. 2 Hyaluronan levels for blood after oral administration in several animals.

Figure 3:
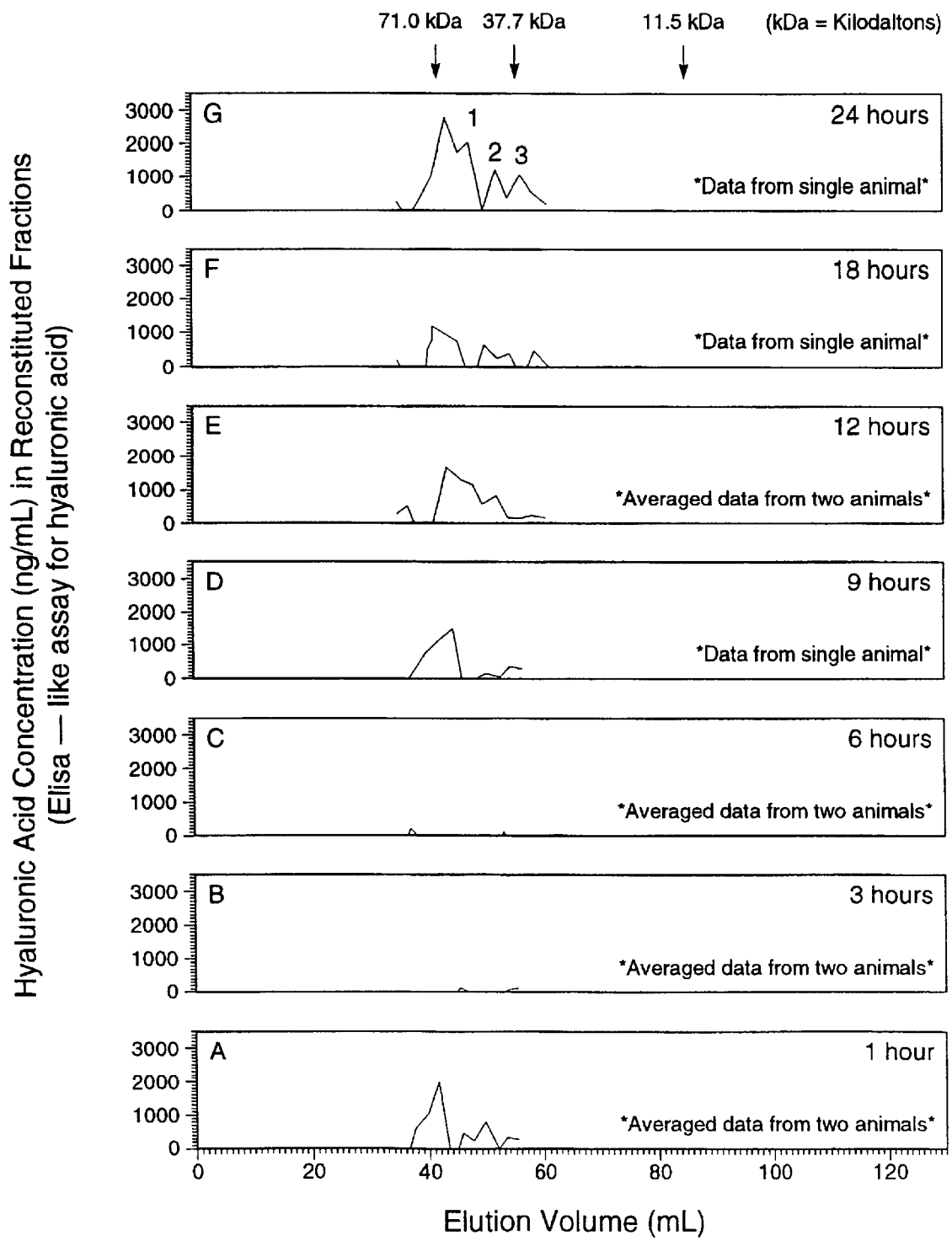
FIG. 3 illustrates Time Course of Rat Serum Hyaluronan (HA) levels after oral administration of sodium hyaluronate at 30 mg/kg, mean average molecular weight distribution of 400,000 daltons (Protein Standard) (2% by weight in solution 30,000 to greater than 70,000 daltons (30→70 kDa)).

FIG. 3 Hyaluronan administered orally to rats appears as a burst of HA in blood one hour after administration, a decrease for five hours followed by a steady increase over the next eighteen hours in a time dependent manner. (Background levels of HA are 1000–1500 ng/ml). Note molecular weight of HA recalls a higher range than in IV administered HA (see FIG. 3).

Figure 5:
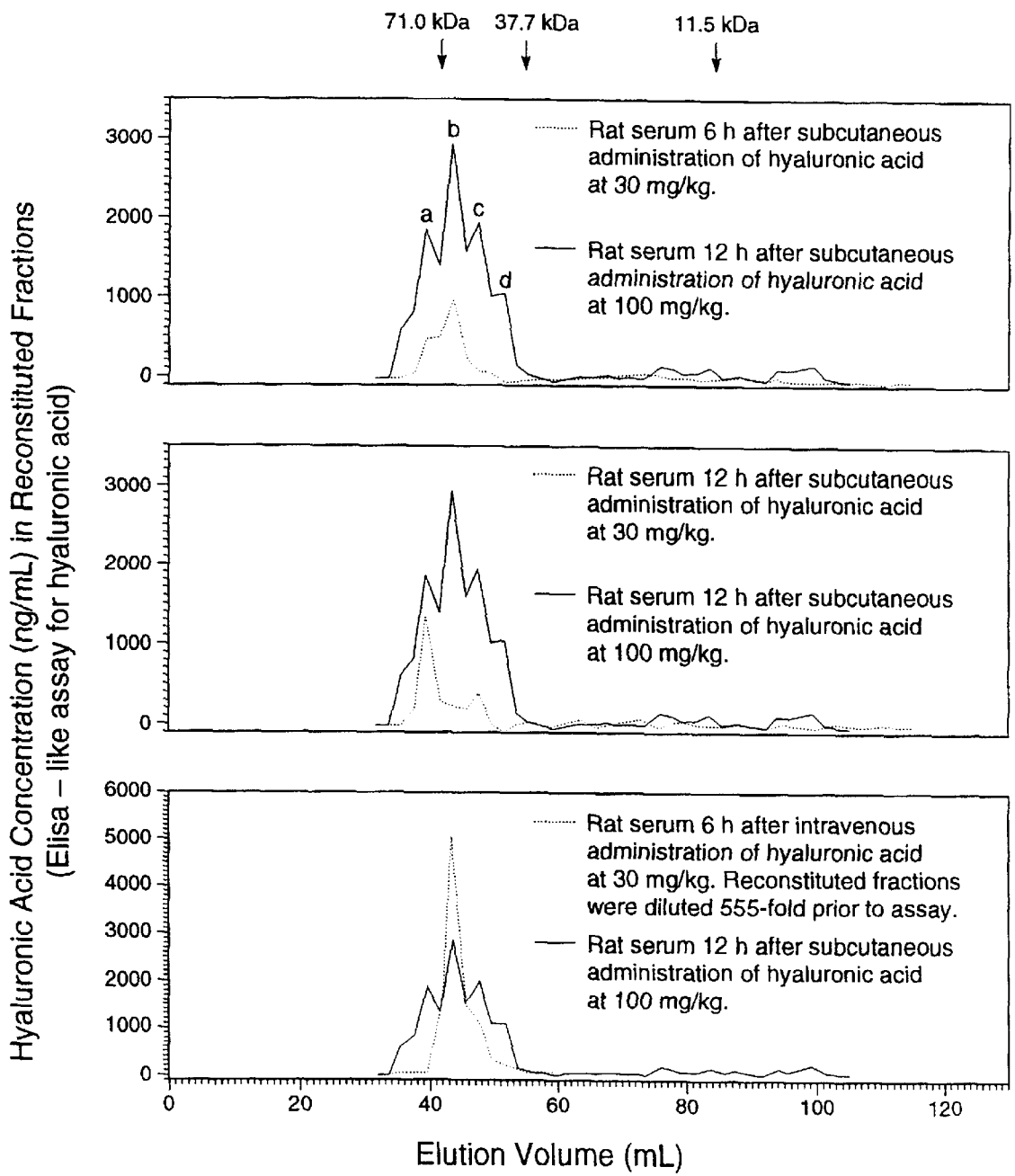
FIG. 5 illustrates Time Course of Subcutaneous and Intravenous administration of HA (same mean average molecular weight distribution) for comparison with oral HA.

FIG. 5 Molecular weight and amounts of HA in blood after subcutaneous administration. Note that the amounts of HA in blood after subcutaneous and oral administration are similar. Also note that in both cases the molecular weight of released HA released from a subcutaneous depot reaches a higher range than that of administered I.V.

Figures 6A, 6B, 6C, 6D:
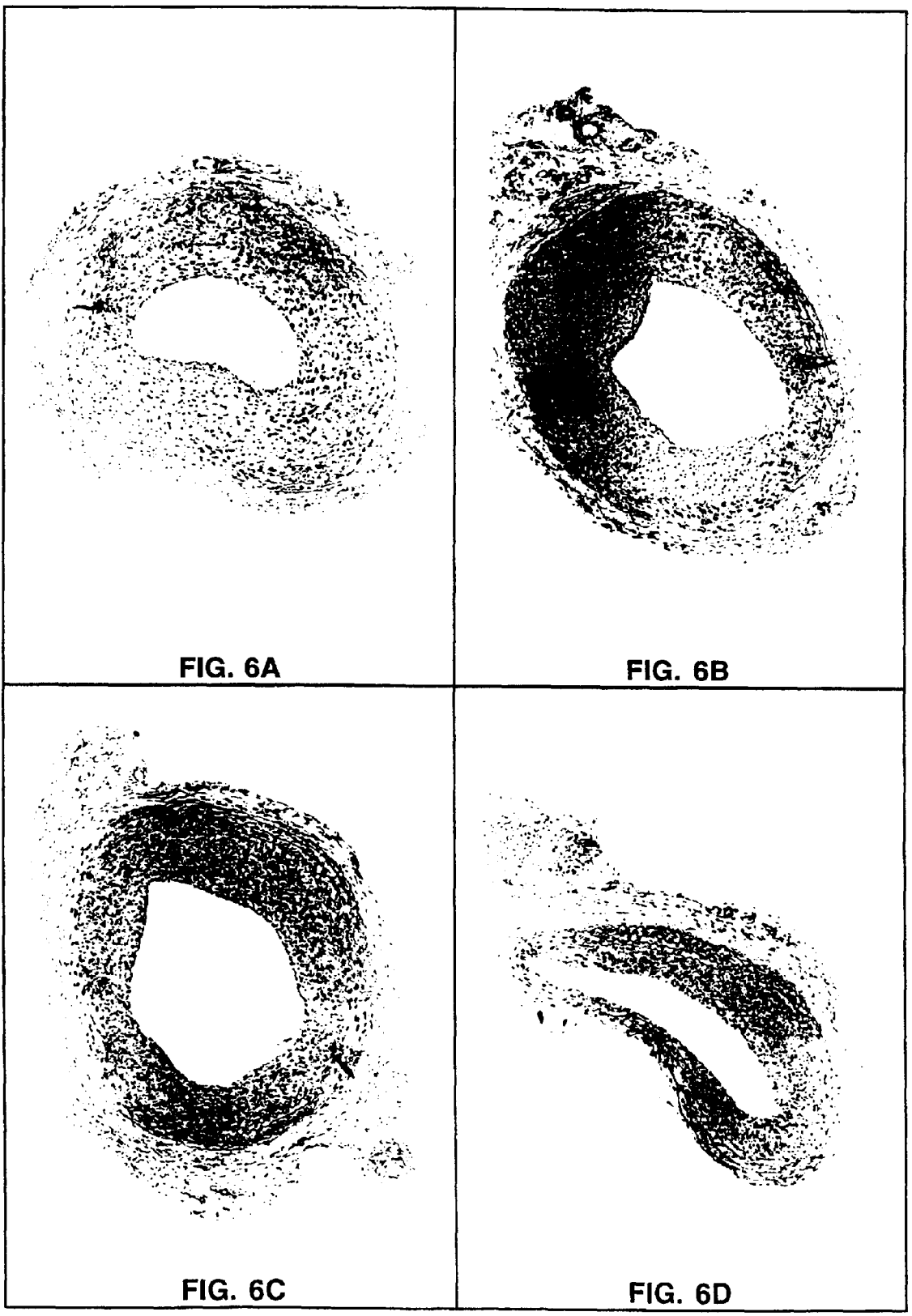
FIG. 6A is a photograph of the cross-section of a rat artery showing the state of the rat artery after balloon angioplasty and after being left to heal on its own.
FIG. 6B is a photograph of the cross-section of a rat artery showing the state of the rat artery after balloon angioplasty, given normal saline orally and left to heal.
FIG. 6C is a photograph of the cross-section of a rat artery showing the state of the rat artery after balloon angioplasty and given orally 1 mg/kg of the body weight of the rat of sodium hyaluronate, 2% by weight solution in sterile water) and left to heal.
FIG. 6D is a photograph of the cross-section of a rat artery showing the state of the rat artery after balloon angioplasty and given orally 3 mg/kg of the body weight of the rat of sodium hyaluronate, 2% by weight solution in sterile water) and left to heal.

FIG. 6 consists of a series of photographs of the cross-sections through carotid arteries of rats showing the effects of different amounts of orally administered Hyaluronan in stenosis of the rat carotid arteries:

All vessels were injured with a fogherty balloon as described in the prior art (Forns et. al., 1994) Cross-sections of arteries of rats treated with HA, saline or left untreated are as shown:

FIG. 6A) no treatment

FIG. 6B) saline treated

FIG. 6C) 1 mg/kg hyaluronan

FIG. 6D) 3 mg/kg hyaluronan

Figures 6E, 6F, 6G:
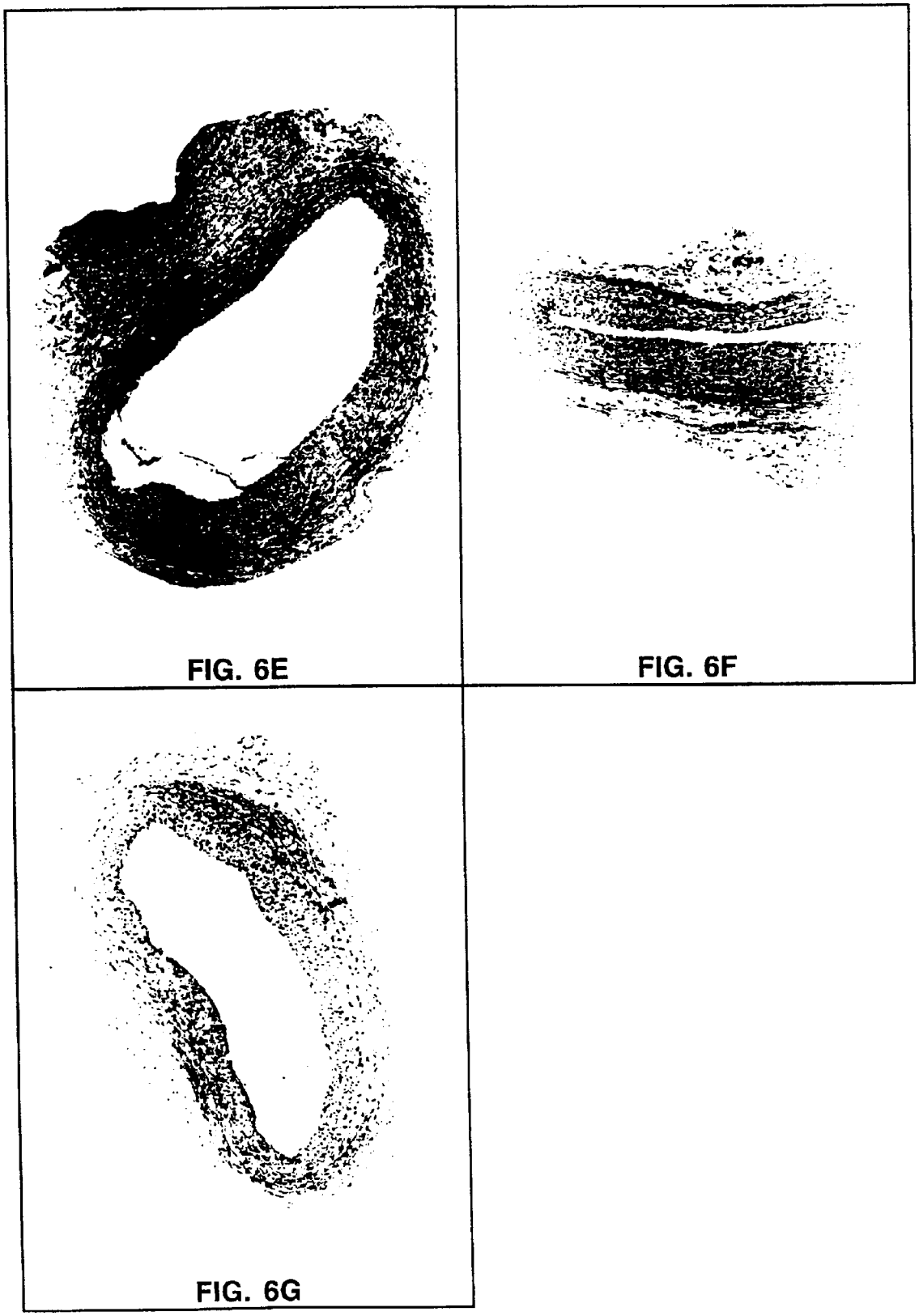
FIG. 6E is a photograph of the cross-section of a rat artery showing the state of the rat artery after balloon angioplasty and given orally 10 mg/kg of the body weight of the rat of sodium hyaluronate, 2% by weight solution in sterile water) and left to heal.
FIG. 6F is a photograph of the cross-section of a rat artery showing the state of the rat artery after balloon angioplasty and given orally 30 mg/kg of the body weight of the rat of sodium hyaluronate (M.W. 400,000 daltons (Protein Standard), 2% by weight solution in sterile water) and left to heal.
FIG. 6G is a photograph of the cross-section of a rat artery showing the state of the rat artery after balloon angioplasty and given orally 100 mg/kg of the body weight of the rat of sodium hyaluronate (M.W. 400,000 daltons (Protein Standard), 2% by weight solution in sterile water) and left to heal. (After healing, each of the rats was sacrificed and the carotid arteries harvested and examined)

FIG. 6E) 10 mg/kg hyaluronan

FIG. 6F) 30 mg/kg hyaluronan

Optimal effects on smooth muscle cell proliferation were noted between about 3–10 mg/kg Hyaluronan oral administration. (The neointima to intima ratios were smaller—see FIG. 7.)

QUANTIFICATION OF WHAT IS SHOWN IN THE PHOTOGRAPHS IN FIGS. 6A–6G

TABLE 1

Effect of orally administered hyaluronan (HA) in stenosis after balloon (angeoplasty) injury of the rat carotid artery. (FIGS. 6A–6G)

| DOSE | N/I RATIO ± S.E.M. (NEOINTIMA /INTIMA RATIO WHERE N IS NEOINTIMA AND I IS INTIMA) |
|---|---|
| (FIG. 6A) No treatment | 2.5 ± 0.9 |
| (FIG. 6B) Saline | 2.8 ± 0.7 |
| (FIG. 6C) 1 mg/kg (HA) | 2.6 ± 0.8 |
| (FIG. 6D) 3 mg/kg (HA) | 1.7 ± 0.4 |
| (FIG. 6E) 10 mg/kg (HA) | 0.4 ± 0.03 |
| (FIG. 6F) 30 mg/kg (HA) | 0.99 ± 0.06 |
| (FIG. 6G) 100 mg/kg (HA) | 1.1 ± 0.08 |

These values represent the mean of, and standard error of the mean (S.E.M.) of, four animals. These experiments were repeated twice with similar results.

Figure 13:
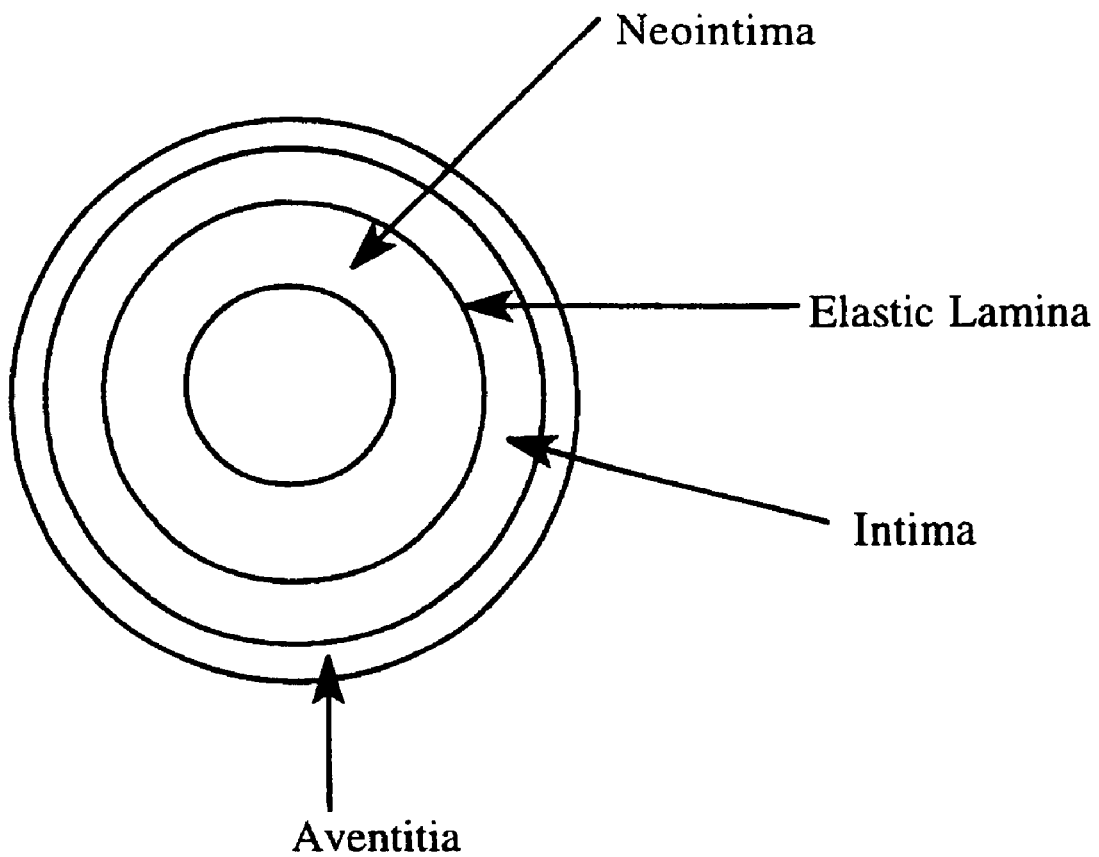

What is shown in each photo represents a cross-section of the rat artery as shown in FIG. 13.

METHODOLOGY

Elisa-Like Assay for Hyaluronic Acid in Column Fractions from Serum Obtained after the Oral Administration of Sodium Hyaluronate at 30 mg/kg (400.000)Daltons Mean Average Molecular Weight Distribution (Protein Standard), 2% by Weight in Sterile Water)

A.) Chromatography
  using 2 mL fraction volumes.
B.) Elisa-Like Assay for Hyaluronic Acid
  Prior to assay the column fractions were prepared in the following manner:
    1900 $\mu$.L of each 2 mL fraction was frozen at—80° C. and then taken to dryness on a speed vac concentrator at room temperature.
    fractions were reconstituted with 125 $\mu$.L of ddH$_2$O and then assayed.
C.) Discussion of Data in FIG. 3

Figure 1:
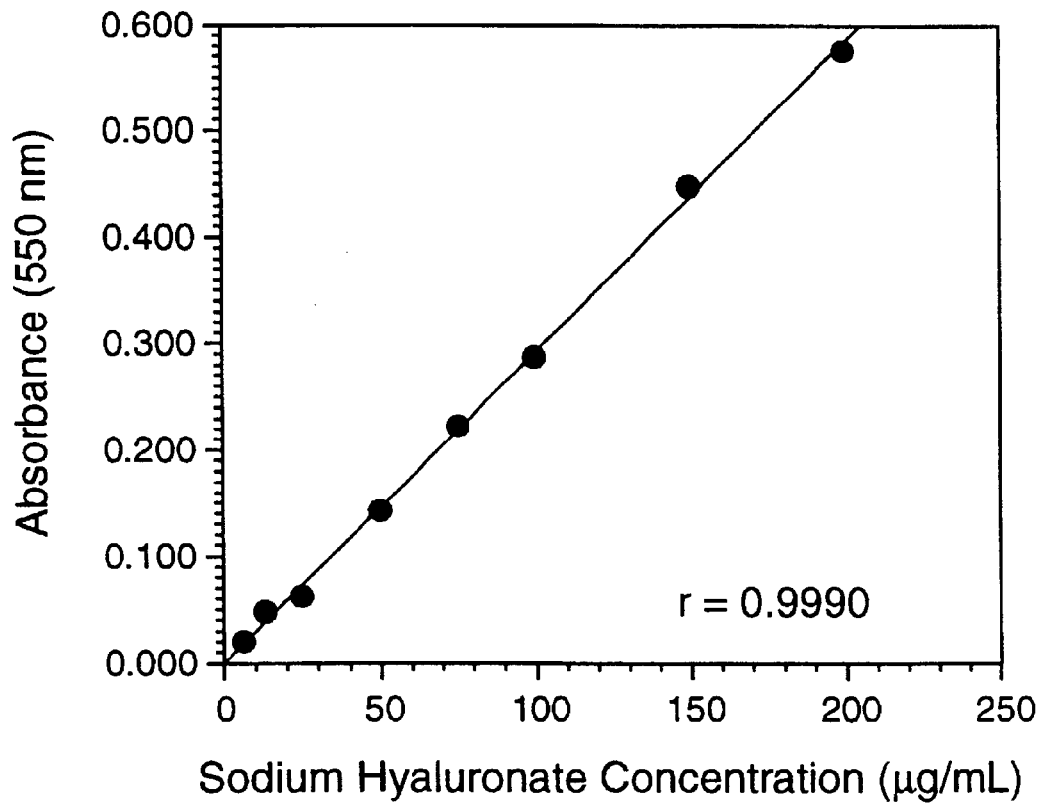
FIG. 1 depicts Aggrecan Assay used for the Determination of standardization of Hyaluronic Acid in plasma.

The data has been summarized in FIG. 3. The results show that the oral administration of sodium hyaluronate, (M.W-750,000 daltons (determined by Protein Standard), 2% by weight in sterile water), at a single dose of 30 mg/kg, results in an increase in serum hyaluronic acid on the order of that seen for the subcutaneous administration of this compound at 30–100 mg/kg. FIG. 3 indicates that serum hyaluronic acid levels are increased within the first hour after oral administration of sodium hyaluronate, followed by a sharp decrease to background levels in normal serum at 3 and 6 hours post-feeding. Serum hyaluronic acid levels are again found to increase at 9 hours post-feeding of HA and this increase is sustained over the time period extending up to 24 hours post-feeding of HA. The sharp drop in serum hyaluronic acid levels seen at 3 and 6 hours post-feeding appears to be a real event since it was reproduced in serum analyzed from two different animals for each time point. The overall trend appears to be satisfactory. It is indicative of an initial absorption of sodium hyaluronate in the stomach (1 hour post-feeding of HA) followed by a rapid clearance of this initial "pulse" from the blood. The second "pulse" of increased serum hyaluronic acid (9–12 hours post-feeding of HA) appears then to represent a second phase of absorption, as the administered sodium hyualuronate moves into the small and large intestine. The majority of serum hyaluronic acid at 1 hour and 9 hours post-feeding of HA (FIG. 3 (A), (D)) elutes in the region of V, indicating a molecular weight >71 kDa(Kilodaltons (high molecular weight species). Between 12–24 hours post-feeding (FIG. 3 (E), (G)), there appears to be an emergence of smaller molecular weight hyaluronic acid species in the molecular weight range between about 30 and about >80 kDa, and more particularly between 71–37.7 kDa (Kilo-daltons (peaks 1,2 and 3 in FIG. 1(G), representing 55.5, 47 and 38 kDa, respectively (Protein Standard). Two assays were used to measure HA in serum: (i) carbazole, and (ii) aggrecan assay.

F: Carbazole Assay for the Determination of Glucuronic Acid
  See enclosed FIG. 6
  Materials
A. Chemicals
  Carbazole (99%): Aldrich Chemical Co., cat. no. C308–1.
  Borax (Sodium Tetraborate.10 H$_2$O): Sigma Chemical Co., prod. no. B-9876).
  Sodium Hyaluronate: Hyal Pharmaceutical Corporation (Applicant)
  H$_2$SO$_4$ (AR) analytical reagent: Mallinckrodt Specialty Chemicals Co.

B. Apparatus

Hot water bath.

Vortex mixer.

12×75 mm disposable glass culture tubes: Fischer Chem. Co., cat. no. 14-958-C.

Visible spectrophotometer or Elisa microplate reader.

96 well, Sarstedt polystyrene microtest plates (For microplate assay): Sarstedt Canada, order no. 82.1581.100.

General Procedure

Prepare a series of hyaluronic acid standards and solutions of 0.025 M sodium tetraborate.$10H_2O$ in concentrated $H_2SO_4$ and 0.125% carbazole in absolute ethanol. For this assay, a linear response has been achieved with hyaluronic acid standards up to 200 μg./mL, (the range of linearity is expected to be extendible to even higher standard concentrations).

Place 3 mL of 0.025 M sodium tetraborate solution in glass tubes and cool thoroughly on ice prior to addition of samples and standards.

Carefully layer (so as to avoid mixing) 0.5 mL of sample or standard over the sodium tetraborate solution in the reaction tubes and place tubes back on ice until all tubes have been prepared.

Mix the contents of each tube thoroughly with a vortex mixer and return the tube to the ice, while mixing the others, to prevent excessive heating of sample.

Place reaction tubes in a 90° C. water bath for 10 minutes and then transfer to a tub of cool water for 5–10 minutes.

Add 100 μ.L of 0.125% carbazole solution to each tube and mix thoroughly with a vortex mixer.

Re-heat the reaction tubes in the 90° C. water bath for an additional 15 minutes. Transfer to a tub of cool water for 5–10 minutes.

Measure absorbance of samples and standards at 530 nm.

Procedure using Microtest Plates (ELISA'S)

For the carbazole reaction, follow general procedure—as outlined; however, the following volume reductions should be introduced into the procedure: 0.5 mL sodium tetraborate solution per tube, 83.3 μ.L. of sample or standard and 16.6 μ.L. of 0.125% carbazole.

After completion of the reaction,transfter 200 μ.L of each sample and standard to individual wells of a 96 well microtest plate. Immediately measure the sample absorbance at 530 ηm (550 ηm, given the available filters with some instruments) using a microplate reader. Biotinylated Aggregcan, an HA binding protein, can be used to detect low levels of HA in serum by in ELISA assay that has been published and is known to persons skilled in the art. This assay is more sensitive than the carbazole assay and was used for conformation.

Figure 8:
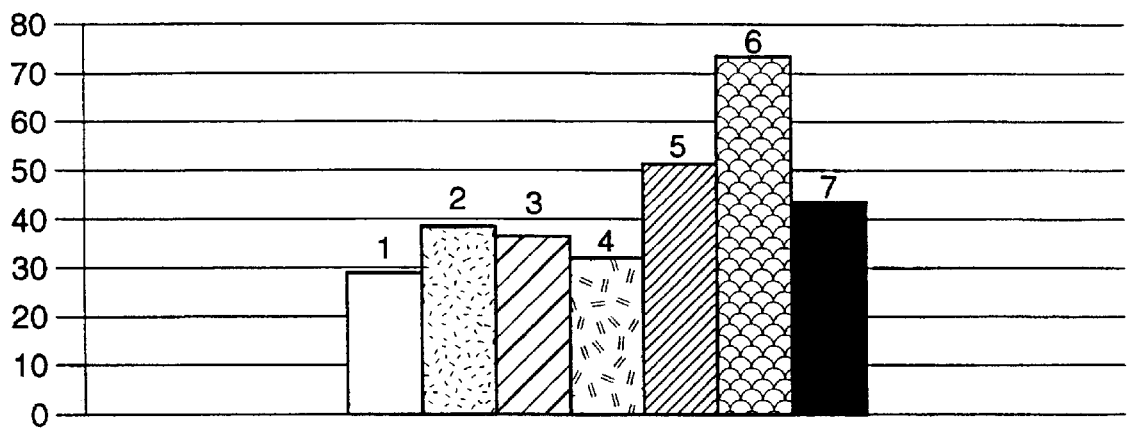
FIG. 8 is a chart depicting MPO content (oral) (MPO—Myleoperoxidase assay) which detects neutrophils

With respect to neutrophil accumulation, reference is to be had to FIG. 8—MPO Content (oral) where MPO is Myleoperoxidase and MPO has been assayed by the methods known to persons skilled in the art. This assay for detecting myleoperoxidase (which is an enzyme) is a good test and thus a good measure for detecting neutrophils.

Thus having regard to FIG. 8, it is clear that the presence of hyaluronic acid (HA) at the site of restenosis, reduces the number of neutrophils. While there appears to be little difference between the bars labelled 1–4, nevertheless there is a substantial difference between those and bars 5–7. It is also clear that the response is phasic (as opposed to a linear dependence—the more hyaluronan, the better the results). In fact the optimal oral administration results appear between about 3 to about 10 mg/kg administered orally.

Figure 4:
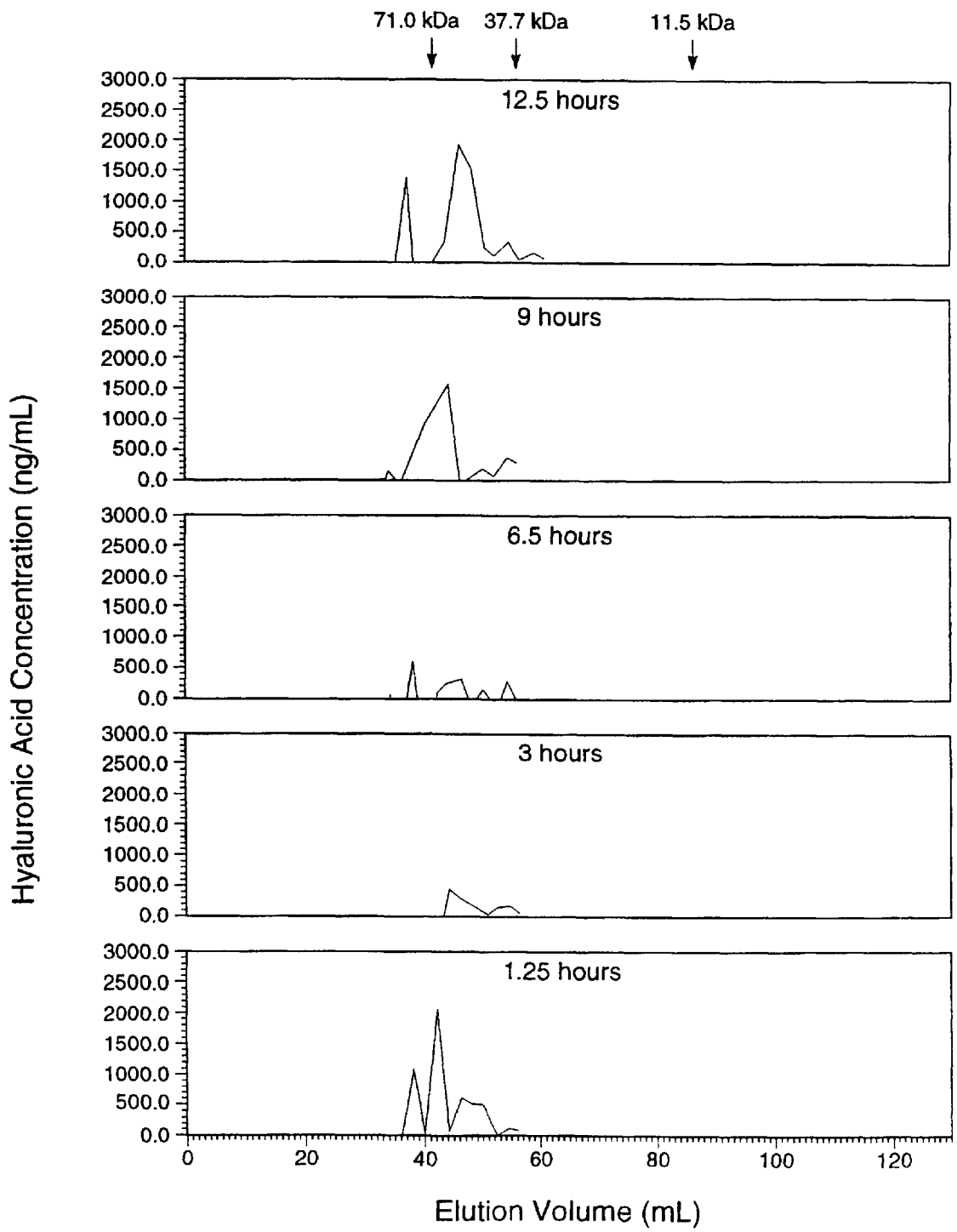
FIG. 4 illustrates Gel Filtration Chromatography of rat serum after oral administration of Hyaluronic Acid administered to each rat at 30 mg of hyaluronan per kilogram of body weight of each rat.

With reference to FIG. 4, (as with FIG. 3), the serum hyaluronan levels after oral administration of hyaluronan to rats increases after about 1.25 hours after administration in rats (m.w. daltons determined by Protein standard) followed by a sharp decrease to background levels in normal serum at 3 and 6 hours post-feeding of HA. Serum hyaluronan levels are again found to increase at 9 hours post feeding of HA, and this increase is sustained over an extended period. Note the molecular weights of the hyaluronan in the serum closely follow molecular weights of the serum hyaluronan identified in FIG. 3.

With reference to FIG. 4, the hyaluronan given orally is initially absorbed in the stomach providing the first pulse, and then as a result of absorption in the small and large intestine, gives a second pulse of hyaluronan in the serum. Hyaluronic acid has previously been shown to be absorbed across the large intestine wall when experimentally perfused in this organ.

Thus it is possible by suitable oral administration of dosages of hyaluronan to provide a sustained release of HA into the body—such as by for example, administration at time 0, followed by a sustaining dosage at 3 hours, then repeated after 24 hours, 48 hours, etc. (see FIG. 3) will provide the sustaining dosage.

Figure 7:
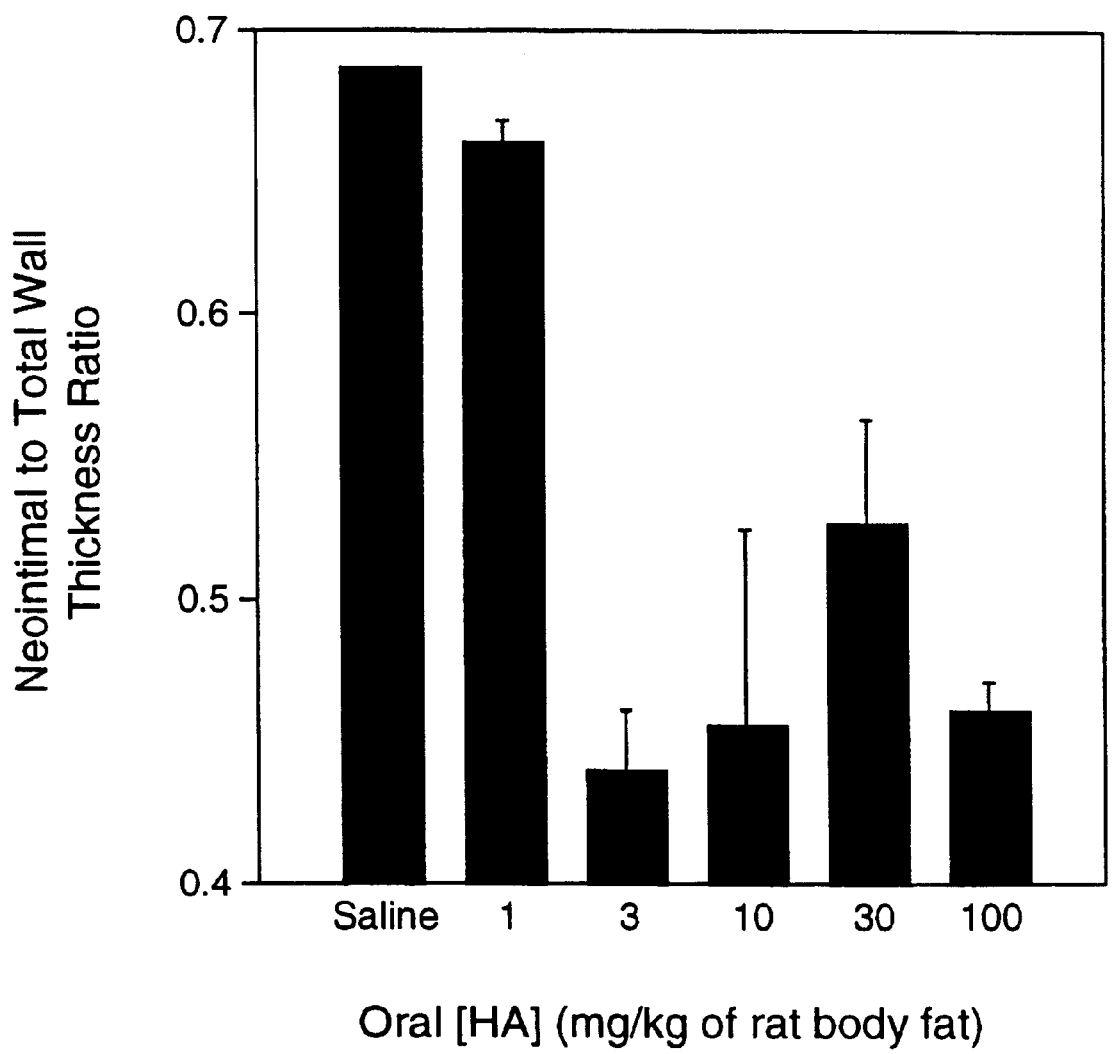
FIG. 7 illustrates the effects of oral hyaluronan administration of various concentration of hyaluronic acid on neointernal formation in rats after balloon angioplasty.

FIG. 7 illustrates the effects of oral administration of HA on Neointimal formation in rats after balloon angioplasty. Six groups of tests were conducted, each test in respect of 3 rats. Thus, the six test results shown in FIG. 8 resulted from the use of 18 rats. It is clear the neointimal to total wall ratio (see illustration at page 18) is greater for administration of saline, followed by the administration of HA in amounts per kilogram of body weight of 1 mg, then 100 mg, 10 mg and 3 mg. This is consistent with the findings illustrated in FIGS. 6 and 8 and the discussion herein.

Figure 11A:
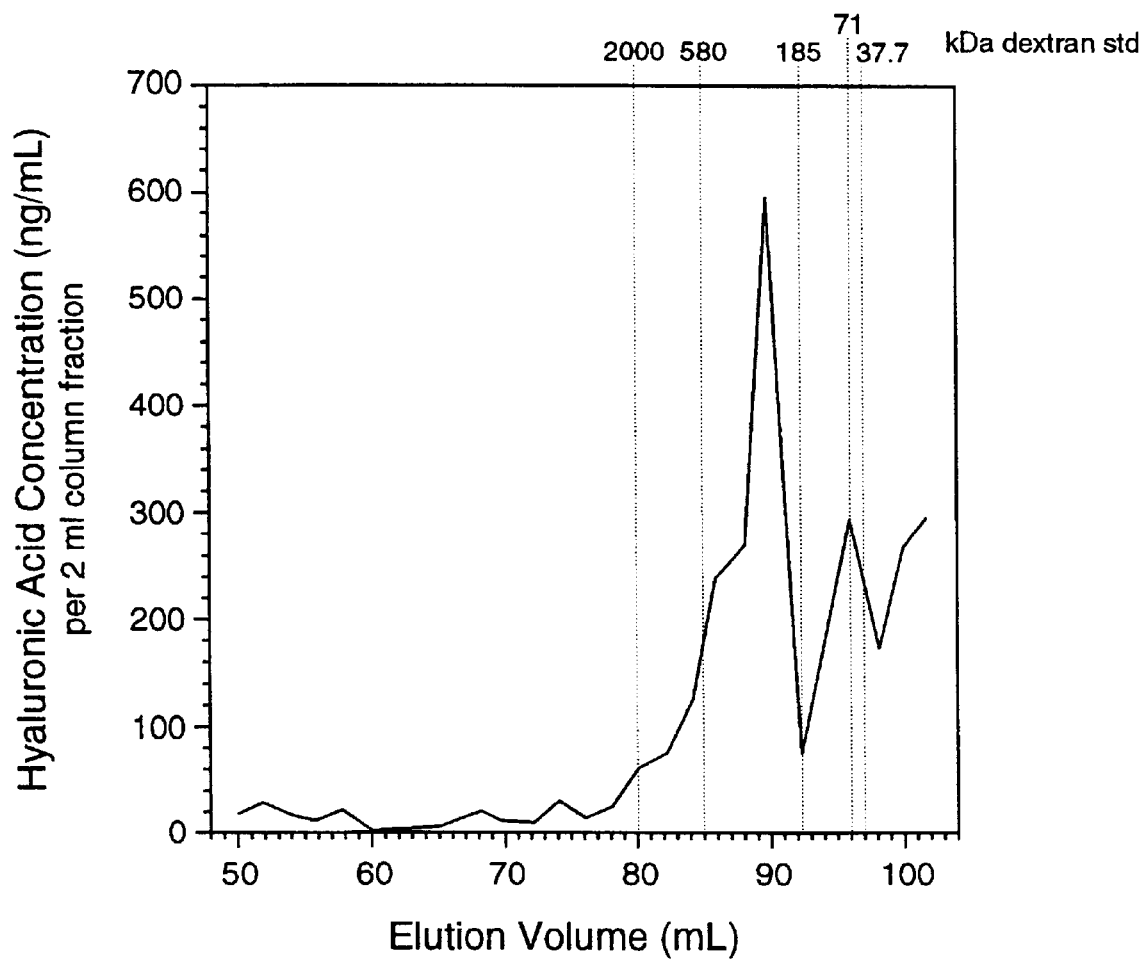
FIGS. 11A, 11B and 11C illustrate molecular weights of hyaluronan determined by Dextran Standard, in three humans orally administered hyaluronan (m.w. less than 500,000 daltons, Dextran Standard).
Figure 11B:
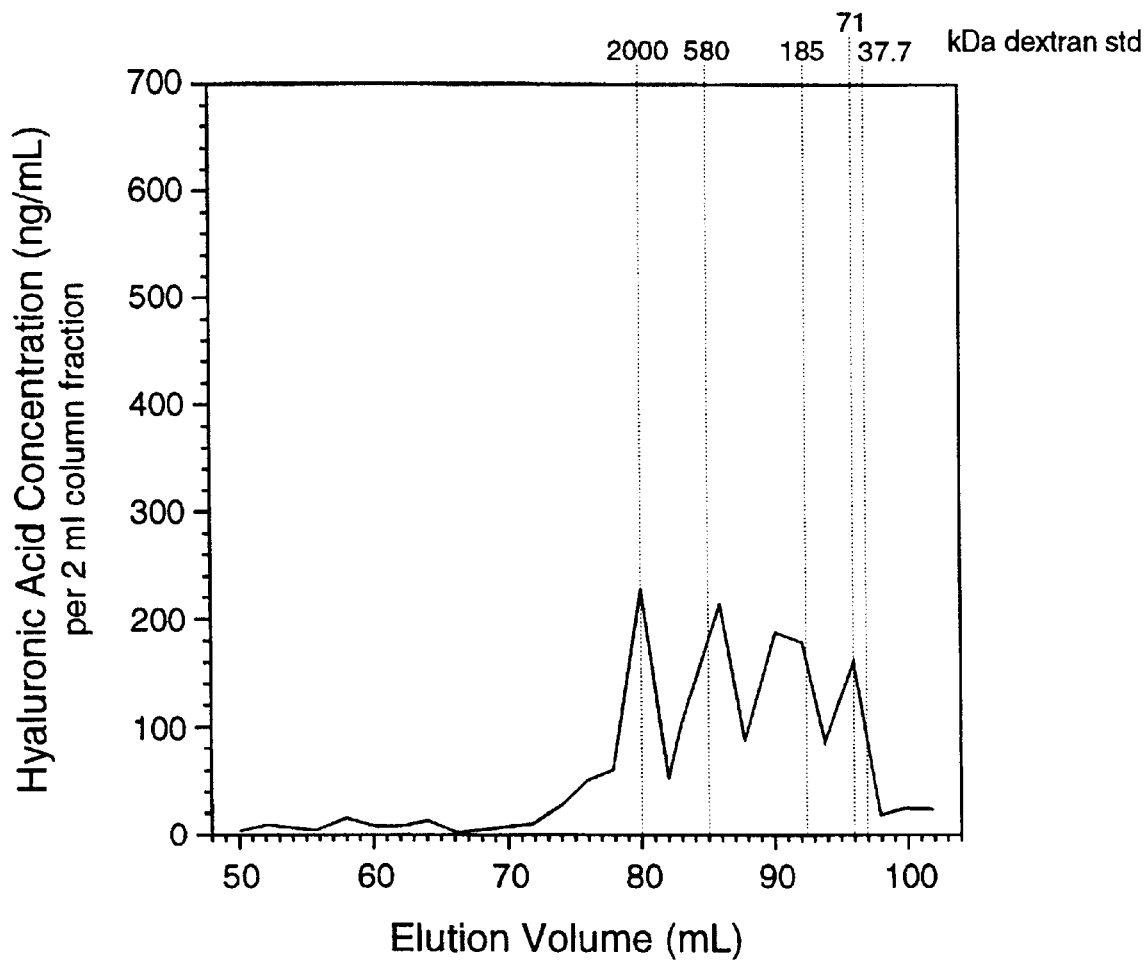
Figure 11C:
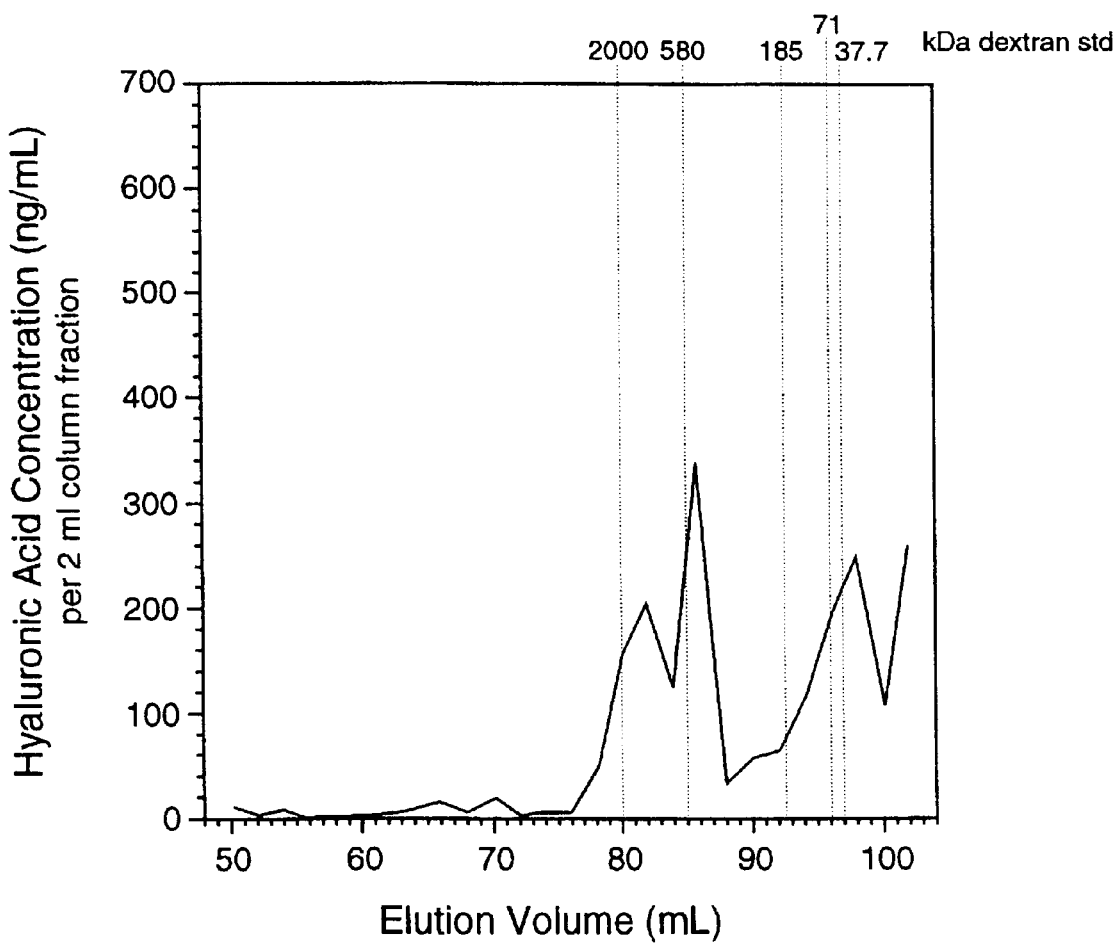

FIGS. 11A, 11B and 11C illustrate the release of amounts of hyaluronic acid into the blood stream of individuals (human) who have taken hyaluronan orally and the molecular weights of the serum hyaluronan released by the bodily processes. The molecular weights of the hyaluronan released into the human blood serum appear to include amounts at peaks between 400,000 daltons and 600,000 daltons such as less than 500,000 daltons, between about 200,000 and about 300,000 such as greater than 200,000 daltons, and between about 30,000 daltons and about 80,000 daltons (determined using the Dextran Standard).

FIGS. 9A, 9B and 9C provide Tables illustrating the amounts of serum hyaluronan in rats at various times after administration of various oral dosages of hyaluronan (3, 10 and 30 mg hyaluronan per kilogram of rat body weight). "M" is the amount [μg/ml, also μg/L); "SD" is the standard deviation and "SE" is the standard error.

Figure 10:
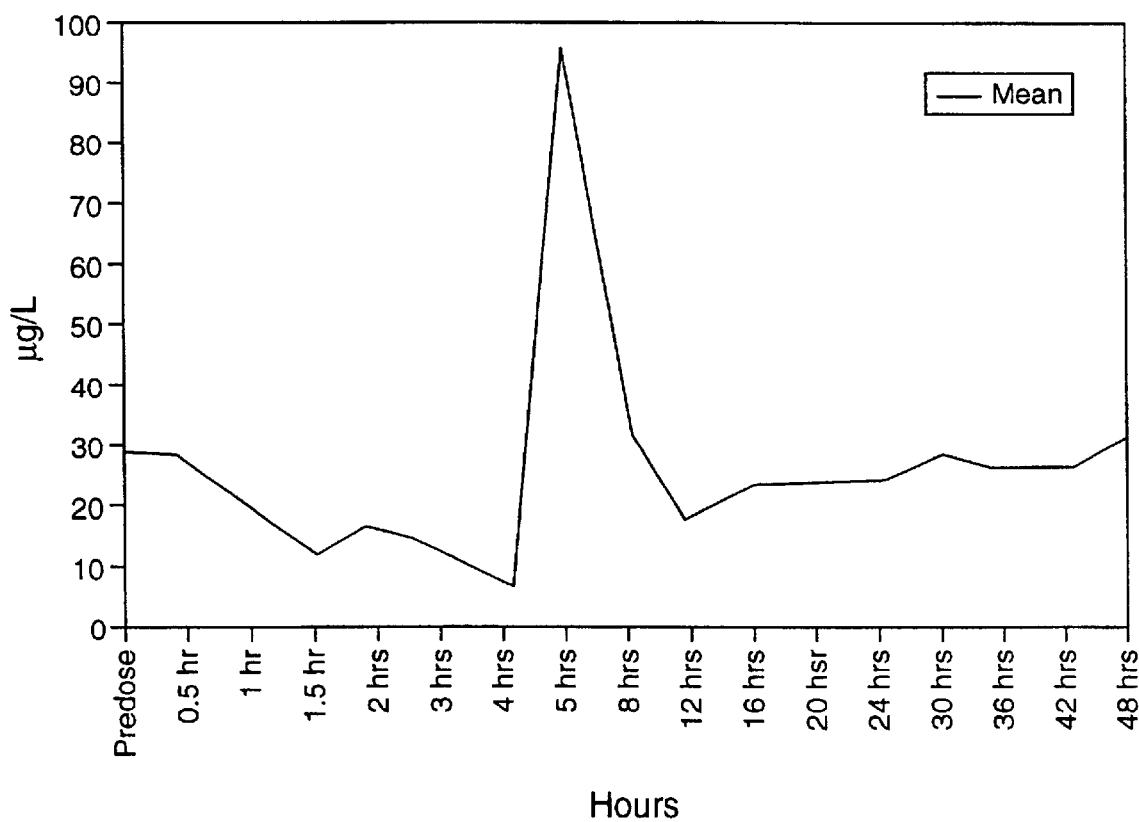
FIG. 10 illustrates serum levels of hyaluronic acid ($\mu$g/ml) following the administration of hyaluronic acid in humans (300 mg/kg of body weight orally (average molecular weight administered less than 750,000 daltons—Protein Standard).

FIG. 10 illustrates the mean serum hyaluronan concentration after giving individual humans oral dosages containing 30.0 mg/kg of hyaluronan (molecular weight less than 750,000 daltons determined by the Protein Standard). The increased serum presence of hyaluronan exhibited increased levels of serum hyaluronan between about hours 4–12.

Thus, a suitable therapeutic regimen for sustained presence and maintenance of therapeutic levels of HA can be provided by orally administering suitable oral dosage amounts of HA (eg. 3–10 mg/kg of body weight of a human in a suitable form (eg. 2% solution in saline or sterile water) for oral administration to provide a therapeutic serum level of HA in the blood such as to inhibit restenosis.

Where medicines or therapeutic agents can be given orally, therapeutically effective amounts of the medicine and therapeutic agents can be administered with the HA. The HA when going into the serum, takes the medicine/therapeutic agent with it into the serum and the medicines/therapeutic agents are transported to the sites in need of treatments (sites for example of trauma, disease focus, pathological tissue, underperfusion, and inflammation expressing excess Hyaluronan (HA) receptors). Thus, suitable therapeutic regimens of treatment can be prepared to provide sustained therapeutic levels of hyaluronan in the body by oral administration (with or without a medicine or therapeutic agent).

These therapeutic sustained levels of hyaluronan can easily be determined from the kinetics of the delivery of hyaluronan into the serum by oral administration of hyaluronan (with or without a therapeutic agent/medicine).

Figure 12A:
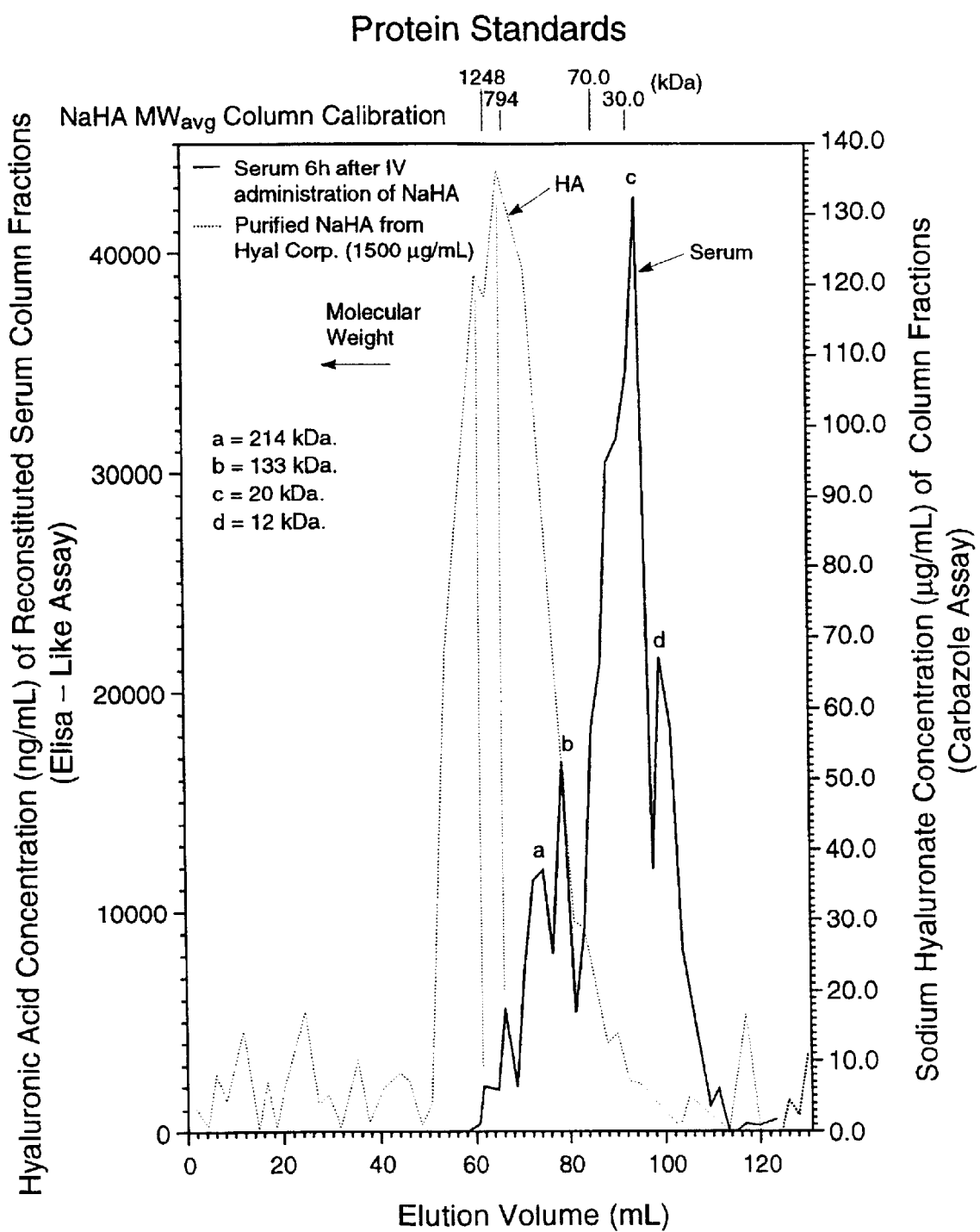

It also appears that where high molecular weight hyaluronan is given orally to a patient, the body reduces the molecular weight of the hyaluronan released into the blood serum to have a lesser molecular weight (for example about 30,000 daltons→80,000 daltons [determined by Protein Standard]). Therefore, giving to a human Hyaluronan, having a mean average molecular weight in the order of between about 30,000 to about 80,000 daltons (Protein Standard), between about 200,000 daltons and about 300,000 daltons (determined by the Dextran Standard), and between about 400,000 daltons and 600,000 daltons (determined by the Dextran Standard), saves the human body from having to reduce the molecular weight of the orally administered hyaluronan. (See for example FIGS. 1, 5, 4 and 11A–C.) FIGS. 12A and 12B each depict standard curves for the same originally administered hyaluronan (HA) whose molecular weight was determined using the weight by Protein Standard (FIG. 12A) and the Dextran Standard (FIG. 12B). The conversion factor from the Molecular Weight Determination by Dextran Standard to the Molecular Weight Determination by the Protein Standard has been calculated from the curves as in the order of about 3.3. To convert the Molecular Weight Determination (Dextran Standard) to Molecular Weight Determination (Protein Standard), one must divide the Molecular Weight of the Dextran Standard by 3.3. To convert the Molecular Weight of the Protein Standard to the Molecular Weight of the Dextran Standard one must multiply the Molecular Weight Protein Standard.

As many changes can be made to the embodiments of the invention without departing from the scope of the invention, it is intended that all material herein be interpreted as illustrative of the invention and not in a limiting sense.

The embodiments of the invention in which an exclusive Property or privilege is claimed are as follows:

1. A method of treating restenosis in a subject in need thereof comprising orally administering to the subject an amount of hyaluronan effective to treat restenosis.

2. The method of claim 1, wherein the hyaluronan has a molecular weight between about 9,000 daltons and 1,000,000 daltons (protein standard).

3. The method of claim 1, wherein the hyaluronan has a molecular weight between about 30,000 daltons and 1,000,000 daltons (protein standard).

4. The method of claim 1, wherein the hyaluronan has a molecular weight between about 80,000 daltons and 1,000,000 daltons (protein standard).

5. The method of claim 1, wherein the hyaluronan has a molecular weight between about 150,000 daltons and 1,000,000 daltons (protein standard).

6. The method of claim 1, wherein the amount of hyaluronan administered is between about 3 and 100 mg/kg body weight.

7. The method of claim 1, wherein the amount of hyaluronan administered is between about 3 and 30 mg/kg body weight.

8. The method of claim 1, wherein the amount of hyaluronan administered is between about 3 and 10 mg/kg body weight.

9. The method of claim 1, wherein the hyaluronan is administered after angioplasty.

10. The method of claim 1, wherein the hyaluronan is hyaluronic acid or a pharmaceutically acceptable salt.

11. A method for inhibiting restenosis in a subject in need thereof comprising orally administering to the subject an amount of hyaluronan effective to inhibit restenosis.

12. The method of claim 11, wherein the hyaluronan has a molecular weight between about 9,000 daltons and 1,000,000 daltons (protein standard).

13. The method of claim 11, wherein the hyaluronan has a molecular weight between about 30,000 daltons and 1,000,000 daltons (protein standard).

14. The method of claim 11, wherein the hyaluronan has a molecular weight between about 80,000 daltons and 1,000,000 daltons (protein standard).

15. The method of claim 11, wherein the hyaluronan has a molecular weight between about 150,000 daltons and 1,000,000 daltons (protein standard).

16. The method of claim 11, wherein the amount of hyaluronan administered is between about 3 and 100 mg/kg body weight.

17. The method of claim 11, wherein the amount of hyaluronan administered is between about 3 and 30 mg/kg body weight.

18. The method of claim 11, wherein the amount of hyaluronan administered is between about 3 and 10 mg/kg body weight.

19. The method of claim 11, wherein the hyaluronan is hyaluronic acid or a pharmaceutically acceptable salt.

20. The method of claim 11, wherein the hyaluronan is administered before, during or after angioplasty.

21. A method of treating stenosis in a subject in need thereof comprising orally administering to the subject an amount of hyaluronan effective to treat stenosis.

22. The method of claim 21 wherein the hyaluronan has a molecular weight between about 9,000 daltons and 1,000,000 daltons (protein standard).

23. The method of claim 21, wherein the hyaluronan has a molecular weight between about 30,000 daltons and 1,000,000 daltons (protein standard).

24. The method of claim 21, wherein the hyaluronan has a molecular weight between about 80,000 daltons and 1,000,000 daltons protein standard).

25. The method of claim 21, wherein the hyaluronan has a molecular weight between about 150,000 daltons and 1,000,000 daltons (protein standard).

26. The method of claim 21, wherein the amount of hyaluronan administered is between about 3 and 100 mg/kg body weight.

27. The method of claim 21, wherein the amount of hyaluronan administered is between about 3 and 30 mg/kg body weight.

28. The method of claim 21, wherein the amount of hyaluronan administered is between about 3 and 10 mg/kg body weight.

29. The method of claim 21, wherein the hyaluronan is hyaluronic acid or a pharmaceutically acceptable salt.

30. A method for decreasing the number of neutrophils at a site of restenosis comprising orally administering to a subject an amount of hyaluronan effective to decrease the number of neutrophils at the site of restenosis in the subject.

31. The method of claim 1, wherein the hyaluronan administered provides hyaluronan in the blood of the subject having a molecular weight of from about 30,000 to about 80,000 daltons (protein standard).

32. A method of treating stenosis in a subject in need thereof comprising orally administering to the subject an amount of hyaluronan effective to treat stenosis.

33. The method of claim 11, wherein the hyaluronan administered provides hyaluronan in the blood of the subject having a molecular weight of from about 30,000 to about 80,000 daltons (protein standard).

34. The method of claim 21, wherein the hyaluronan administered provides hyaluronan in the blood of the subject having a molecular weight of from about 30,000 to about 80,000 daltons (protein standard).

35. The method of claim 30, wherein the hyaluronan administered provides hyaluronan in the blood of the subject having a molecular weight of from about 30,000 to about 80,000 daltons (protein standard).

* * * * *